US00PP23668P2

(12) United States Plant Patent
Zaiger et al.

(10) Patent No.: US PP23,668 P2
(45) Date of Patent: Jun. 18, 2013

(54) INTERSPECIFIC TREE NAMED 'GLORY RED'

(50) Latin Name: **Interspecific *Prunus* species**
Varietal Denomination: Glory Red

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 62 days.

(21) Appl. No.: 13/373,793

(22) Filed: Dec. 1, 2011

(51) Int. Cl.
*A01H 5/00* (2006.01)

(52) U.S. Cl.
USPC ..... Plt./180

(58) Field of Classification Search
USPC ..... Plt./180
See application file for complete search history.

*Primary Examiner* — Annette Para

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1) Vigorous, upright tree growth.
2) Heavy and regular bearer of large size fruit.
3) Fruit with very good flavor and eating quality.
4) Fruit with an attractive dark red skin color.
5) Fruit with good handling and shipping quality.
6) Fruit with an average Brix of 20.0° and a good balance between acid and sugar.

1 Drawing Sheet

Botanical designation: Interspecific *Prunus* species.
Variety denomination: 'Glory Red'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

2. Prior Varieties

Among the existing varieties of plum and interspecific trees, which are known to us, and mentioned herein, 'Laroda' Plum (non-patented), 'Queen Ann' Plum (non-patented), 'Burmosa' Plum (non-patented), 'Flavorfall' Interspecific (U.S. Plant Pat. No. 11,990), 'Red Beaut' Plum (U.S. Plant Pat. No. 2,539), 'Mariposa' Plum (U.S. Plant Pat. No. 111), the proprietary plumcots '4G1180' and '42GA580', and the proprietary apricot×peach '10W100' and the proprietary interspecific seedlings '30M591' and '160LM295', all of the proprietary seedlings are non-patented.

STATEMENT REGARDING FEDERALLY SPONSORED RESEARCH AND DEVELOPMENT

Not applicable.

ORIGIN OF THE VARIETY

The new and distinct interspecific tree was originated by us from crosses between the following species [*Prunus salicina*×(*Prunus salicina*×*Prunus armeniaca*)×(*Prunus armeniaca*×*Prunus persica*)]. It originated as a first generation seedling from the cross of our proprietary interspecific seedlings '30M591' (non-patented) and '160LM259' (non-patented). The seed parent '30M591' (non-patented) was developed by us from multiple crosses between the following varieties; 'Laroda' Plum (non-patented), 'Queen Ann' Plum (non-patented), 'Burmosa' Plum (non-patented), 'Red Beaut' Plum (U.S. Plant Pat. No. 2,539), 'Flavorfall' Interspecific (U.S. Plant Pat. No. 11,990) and our proprietary plumcot '4G1180' (non-patented). The pollen parent '160LM295' (non-patented) was developed by us from multiple crosses of the following varieties; 'Mariposa' Plum (U.S. Plant Pat. No. 111), 'Red Beaut' Plum (U.S. Plant Pat. No. 2,539), the proprietary (non-patented) plumcot selections '4G1180' and '42GA580', and the proprietary peach×apricot selection '10W100' (non-patented). We budded a large number of these seedlings to older 'Nemaguard' Rootstock (non-patented) trees to induce earlier fruit production for evaluation. Under close and careful observation the present seedling exhibited desirable fruit and tree characteristics and was selected in 2009 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree which includes [(Plum×Plumcot)×(Apricot×Peach)] is of large size, vigorous upright growth and a productive and regular bearer of large size, red flesh fruit with very good flavor and eating quality. The fruit is further characterized by having attractive dark red skin color, firm flesh with good storage and shipping quality. In comparison to its seed parent '30M591' (non-patented) the fruit of the new variety is approximately 30 days later in maturity. In comparison to its pollen parent '160LM295' (non-patented) the fruit of the new variety has a brighter red skin color and is approximately 20 days later in maturity. In comparison to the commercial variety 'Flavorfall' Interspecific (U.S. Plant Pat. No. 11,990) the fruit of the new variety has red flesh compared to yellow and is approximately 27 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 4 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 4 year old specimens grown near Modesto, Calif., with color in accordance with Munsell Book of Color.

Tree:

*Size*.—Large, pruned to 3 to 3.5 meters in height and width for economical harvesting of fruit, varies with different cultural practices.

*Vigor*.—Vigorous, growth of 1.5 to 2 meters the first growing season, varies with type and fertility of soil, climatic conditions and cultural practices.

*Form*.—Upright, usually pruned to vase shape to allow more sunlight to center of tree to enhance fruit color and health of fruit spurs.

*Branching habit*.—Upright, crotch angle approximately 35°, increases with crop load.

*Productivity*.—Productive, thinning and spacing of fruit necessary for desired market size.

*Bearer*.—Regular, adequate fruit set 3 consecutive years. No alternate bearing observed.

*Fertility*.—Self-sterile, pollinators required.

*Density*.—Medium dense, usually pruned to vase shape, improves new spur growth and enhances fruit color.

*Hardiness*.—Hardy in all stone fruit growing areas of California. Tree grown in USDA Hardiness Zone 9. Winter chilling requirement approximately 750 hours at or below 45° F.

Trunk:

*Size*.—Medium to large. Average circumference 46.9 cm at 31.0 cm above ground level.

*Stocky*.—Medium stocky.

*Texture*.—Medium shaggy, roughness increases with age of tree.

*Color*.—Varies from 5Y 7/2 to 5Y 6/2.

Branches:

*Size*.—Medium. Average circumference 10.8 cm at 1.2 meters above ground. Crotch angle approximately 35°, increases with heavy crop load.

*Surface texture*.—New growth relatively smooth. Mature growth medium rough, roughness increases with age.

*Lenticels*.—Size — medium. Average number 39 in a 25.8 sq cm area. Average length 3.5 mm. Average width 0.5 mm. Color varies from 7.5YR 5/10 to 5YR 5/10.

*Color*.—New growth varies from 10Y 4/4 to 2.5GY 4/6. Old growth varies from 2.5Y 3/4 to 10YR 3/4, varies with age of growth.

Leaves:

*Size*.—Medium. Average length 99.1 mm. Average width 39.6 mm.

*Form*.—Obovate.

*Apex*.—Acuminate.

*Base*.—Cuneate.

*Margin*.—Serrulate.

*Thickness*.—Medium.

*Surface texture*.—Upper surface relatively smooth, slight indentations over midrib and leaf veins, glabrous. Lower surface relatively smooth, except for small ridges created by midrib and pinnate venation, glabrous.

*Petiole*.—Average length 15.2 mm. Average width 1.6 mm. Longitudinally grooved. Color varies from 5GY 6/6 to 5GY 6/8. Surface — glabrous.

*Glands*.—Type — globose. Size — small. Average length 0.1 mm. Average diameter 0.1 mm. Average number 2, varies from 1 to 2. Located on the base of the leaf blade and upper portion of the petiole. Color varies from 5GY 7/6 to 5GY 7/8.

*Stipules*.—Average number 2. Average length 7.4 mm. Margin — pectinate. Color varies from 5GY 7/6 to 5GY 7/8.

*Color*.—Upper surface varies from 5GY 4/4 to 5GY 3/4. Lower surface varies from 5GY 5/4 to 5GY 4/4. Midvein color varies from 5GY 7/6 to 5GY 6/6.

Flower buds:

*Size*.—Small to medium. Average length 8.7 mm. Average diameter 4.9 mm.

*Hardiness*.—Hardy with respect to California winters.

*Form*.—Conical, becoming elongated just before opening.

*Pedicel*.—Small to medium. Average length 6.7 mm. Average width 0.8 mm. Surface — glabrous. Color varies from 10Y 7/6 to 2.5GY 7/8.

*Color*.—N 9.5/(white).

*Number of buds per spur*.—Average number 10, varies from 9 to 12. Varies with age of spur.

Flowers:

*Date of first bloom*.—Feb. 26, 2011.

*Date of petal fall*.—Mar. 7, 2011, varies slightly with climatic conditions.

*Size*.—Medium. Average height 9.4 mm. Average diameter 18.9 mm.

*Petals*.—Normally 5, alternately arranged to sepals. Size — medium. Average length 8.7 mm. Average width 6.7 mm. Form varies from globose to slightly elongated. Margin — sinuate. Color N 9.5/(white). Both upper and lower surfaces glabrous.

*Sepals*.—Normally 5, alternately arranged to the petals. Size — small. Average length 2.3 mm. Average width 2.1 mm. Shape — triangular, apex rounded. Margin — entire. Both upper and lower surfaces glabrous. Color — upper surface varies from 2.5GY 7/6 to 2.5GY 7/8. Lower surface varies from 10Y 7/6 to 2.5GY 7/6.

*Stamens*.—Average number 28. Average filament length 8.5 mm. Filament color N 9.5/(white). Anther color varies from 5Y 8/8 to 5Y 8/10.

*Pollen*.—Present, self sterile, pollinator required. Color varies from 2.5Y 7/12 to 5Y 7/12.

*Pistil*.—Normally 1. Surface — glabrous. Average length 7.4 mm. Position of stigma average of 1.4 mm below anthers. Color varies from 10Y 8.5/6 to 10Y 8/6.

*Fragrance*.—Heavy aroma.

*Color*.—N 9.5/(white).

*Number flowers per flower bud*.—Average 2, varies from 1 to 3.

*Pedicel*.—Average length 7.5 mm. Average width 0.8 mm. Color varies from 10Y 7/6 to 2.5GY 7/8. Surface — glabrous.

Fruit:

*Maturity when described*.—Firm ripe.

*Date of first picking*.—Sep. 4, 2011.

*Date of last picking*.—Sep. 12, 2011, varies slightly with climatic conditions.

*Size*.—Large. Average diameter axially 56.5 mm. Average transversely in suture plane 63.3 mm. Average weight 156.2 grams, average weight varies slightly with fertility of the soil, amount of thinning and climatic conditions.

*Form*.—Globose.

*Suture*.—Slightly lipped, extends from base to apex.

*Ventral surface*.—Slightly lipped.

*Apex*.—Slightly retuse.

*Base*.—Flat to slightly retuse.

*Stem cavity*.—Rounded to slightly elongated in suture plane. Average depth 5.0 mm. Average diameter 5.1 mm.

Stem:

*Size*.—Medium. Average length 14.3 mm. Average diameter 1.6 mm.

*Color*.—Varies from 7.5Y 6/6 to 10Y 6/6.

Flesh:

*Ripens*.—Evenly.

*Texture*.—Firm, meaty.

*Fibers*.—Few, small, tender.

*Firmness*.—Good, comparable to other commercial varieties.

*Aroma*.—Moderate.

*Amydgalin*.—Undetected.

*Eating quality*.—Very good.

*Flavor*.—Very good, good balance between acid and sugar.

*Juice*.—Heavy, enhances flavor.

*Brix*.—Average Brix 20.0°, varies slightly with amount of fruit per tree and climatic conditions.

*Color*.—Red/yellow, varies from 5R 4/10 to 2.5Y 8/4.

*Pit cavity*.—Average length 23.9 mm. Average width 17.5 mm. Average depth 6.5 mm. Color varies from 5R 3/4 to 5R 2/6.

Skin:

*Thickness*.—Medium.

*Surface*.—Relatively smooth.

*Bloom*.—Moderate amount.

*Tendency to crack*.—None.

*Color*.—Ground color green/yellow, varies from 2.5Y 6/4 to 2.5Y 7/4. Overspread with 2.5R 3/6 to 5R 2/4.

*Tenacity*.—Tenacious to flesh.

*Astringency*.—Undetected.

Stone:

*Type*.—Clingstone.

*Size*.—Medium. Average length 22.4 mm. Average width 15.8 mm. Average thickness 10.9 mm.

*Form*.—Ovoid.

*Base*.—Rounded, some stones flat.

*Apex*.—Pointed. Average length 1.3 mm.

*Surface*.—Very small pits throughout.

*Sides*.—Unequal, one side extending further outward from suture plane.

*Ridges*.—A small narrow ridge on each side of suture extending from base to apex.

*Tendency to split*.—None.

*Color*.—Varies from 2.5Y 7/6 to 10YR 6/6 when dry.

Kernel:

*Size*.—Small to medium. Average length 13.4 mm. Average width 10.3 mm. Average depth 6.6 mm.

*Form*.—Ovoid.

*Viability*.—Viable, complete embryo development.

*Skin color*.—Varies from 2.5Y 8/6 to 2.5Y 7/6.

Use: Dessert.

*Market*.—Local and long distance.

Keeping quality: Good, held firm in cold storage for 3 weeks at 38° to 42° F. without shriveling, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

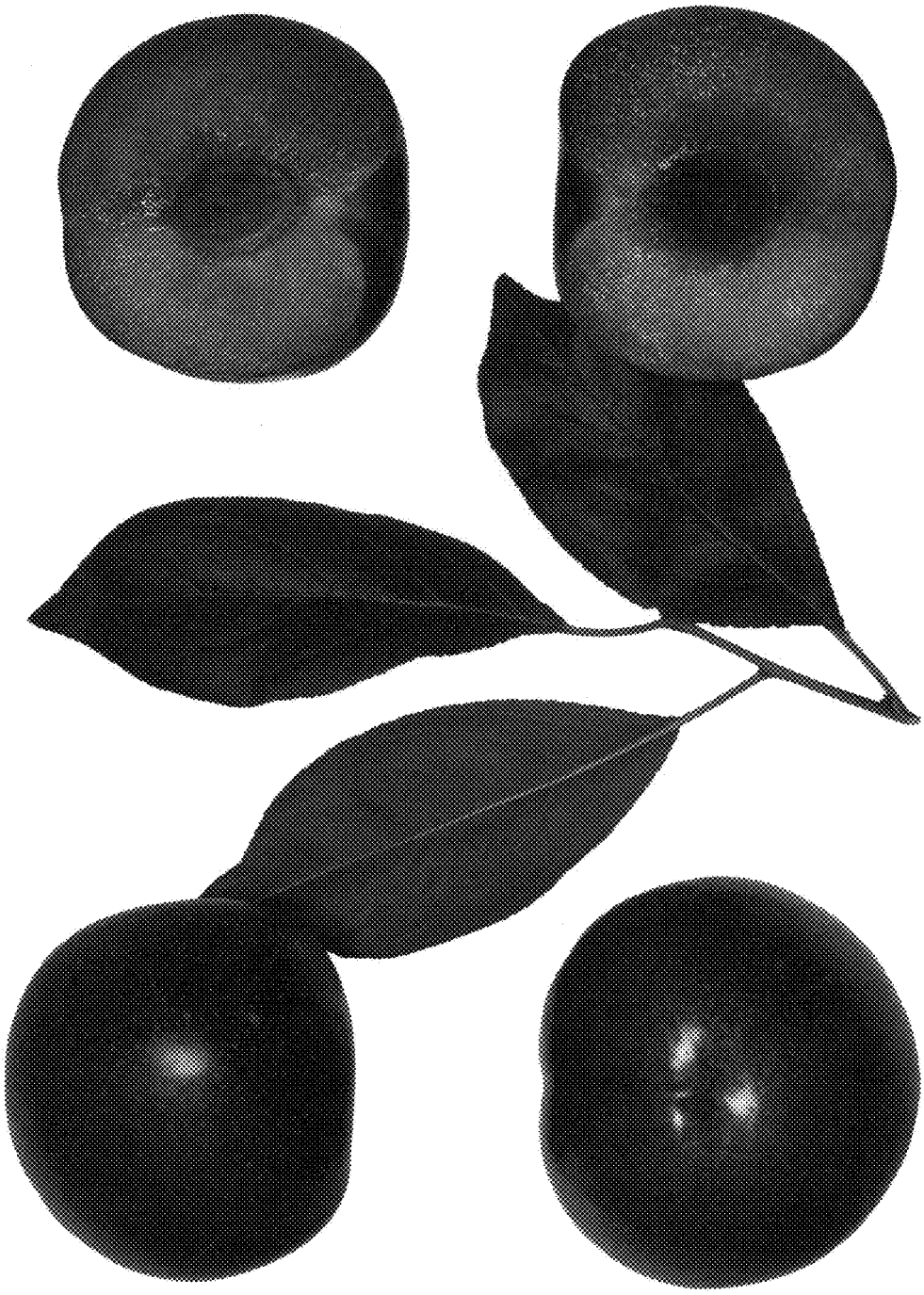

* * * * *